US007758574B2

(12) United States Patent
Hijii et al.

(10) Patent No.: US 7,758,574 B2
(45) Date of Patent: Jul. 20, 2010

(54) ELECTRIC SURGERY APPARATUS FOR SUPPLYING ELECTRIC POWER SUITABLE FOR SUBJECT TISSUE

(75) Inventors: Kazuya Hijii, Tama (JP); Shinji Hatta, Hachioji (JP); Tsuyoshi Hayashida, Sagamihara (JP); Masahide Ohyama, Hino (JP); Kenji Harano, Hachioji (JP)

(73) Assignee: Olympus Corporation, Tokyo (JP)

( * ) Notice: Subject to any disclaimer, the term of this patent is extended or adjusted under 35 U.S.C. 154(b) by 422 days.

(21) Appl. No.: 10/761,960

(22) Filed: Jan. 21, 2004

(65) Prior Publication Data

US 2004/0172111 A1 Sep. 2, 2004

(30) Foreign Application Priority Data

Jan. 29, 2003 (JP) ............... 2003-020957

(51) Int. Cl.
*A61B 18/18* (2006.01)
(52) U.S. Cl. .......................... 606/34; 606/42
(58) Field of Classification Search ................. 607/101; 606/41, 32–35, 42, 48–50
See application file for complete search history.

(56) References Cited

U.S. PATENT DOCUMENTS

| 6,033,399 | A | * | 3/2000 | Gines | ........................... | 606/38 |
| 6,210,403 | B1 | * | 4/2001 | Klicek | ........................ | 606/34 |
| 6,398,779 | B1 | * | 6/2002 | Buysse et al. | ................. | 606/34 |
| 6,511,478 | B1 | * | 1/2003 | Burnside et al. | .............. | 606/41 |
| 6,843,789 | B2 | * | 1/2005 | Goble | ......................... | 606/41 |

FOREIGN PATENT DOCUMENTS

| JP | 2002-65690 | 3/2002 |
| JP | 2002-65691 | 3/2002 |
| JP | 2002-65693 | 3/2002 |

\* cited by examiner

*Primary Examiner*—Michael Peffley
(74) *Attorney, Agent, or Firm*—Scully, Scott, Murphy & Presser, P.C.

(57) ABSTRACT

A high frequency cauterizing power supply unit includes a control circuit for controlling a power supply circuit and waveform generating circuit. The control circuit includes a timer for measuring an output period and pause period, and a counter for measuring the number of times of output. The control circuit detects a setting power and the number of times of output according to the diameter of a blood vessel with a simple method in a short period of time, and controls the output period so as to be shortened, and also controls a setting power and the number of times of output depending on the diameter of the blood vessel.

2 Claims, 7 Drawing Sheets

ELECTRIC SURGERY APPARATUS FOR SUPPLYING ELECTRIC POWER SUITABLE FOR SUBJECT TISSUE

This application claims benefit of Japanese Application No. 2003-20957 filed in Japan on Jan. 29, 2003, the contents of which are incorporated by this reference.

BACKGROUND OF THE INVENTION

1. Field of the Invention

The present invention relates to an electric surgery apparatus, and more particularly to an electric surgery apparatus of which feature is a specific output control portion for controlling a high frequency current.

2. Description of the Related Art

In general, electric surgical equipment such as electric scalpels is used to incise or coagulate living-body tissue, to stop bleeding, or to perform other treatment when surgery or internal surgery is conducted.

Such electric surgical equipment comprises a high frequency cauterizing power supply unit and a treatment device connected to this high frequency cauterizing power supply unit, and conducts the aforementioned treatment by having the treatment device come into contact with a patient and supplying a high frequency current to the patient from the high frequency cauterizing power supply unit.

As for usages of the above-described electric surgery apparatuses, there is a function to seal a blood vessel prior to the operation in order to prevent the blood vessel from hemorrhaging at the time of severing the blood vessel. A strong force for sealing the blood vessel is important in this function, which prevents recurrent hemorrhaging of the severed portion of the blood vessel.

Improving the force for sealing the blood vessel requires increasing of energy to be administered into the tissue at the severed portion. Conventional methods can increase high frequency electric power or prolong the output period to increase energy, however, if unsuccessful, the tissue may adhere to electrodes or be carbonized, thereby adversely deteriorating the sealing force in some cases.

In order to solve this problem, in Japanese Unexamined Patent Application Publication No. 2002-65690, a technique is disclosed wherein energy is administered into the tissue while preventing the tissue from adhering to electrodes or from being carbonized by controlling high frequency electric power so as to repeat output/pausing thereof.

SUMMARY OF THE INVENTION

The present invention has been made in light of the above-described current situation, and accordingly, it is an object thereof to provide an electric surgery apparatus capable of controlling set electric power and the number of times of output depending on the diameter of a blood vessel.

The electric surgery apparatus according to the present invention comprises a high frequency power generating unit capable of generating high frequency power for treatment of living-body tissue, a treatment unit capable of treating the living-body tissue based on the high frequency power generated from the high frequency power generating unit, an intermittent output control unit for controlling intermittent output of the high frequency power, a subject tissue determining unit for determining subject tissue based on change in the high frequency power supplied to the treatment unit, and an intermittent output setting unit capable of setting output values and the number of times of output controlled by the intermittent output control unit based on the determined results of the subject tissue determining unit.

Other features and advantages of the present invention will become more fully apparent in the following description.

BRIEF DESCRIPTION OF THE DRAWINGS

FIGS. 1 through 5 relate to a first embodiment of the present invention, wherein

FIGS. 6 and 7 relate to a second embodiment according to the present invention, wherein

DESCRIPTION OF THE PREFERRED EMBODIMENTS

First Embodiment (Configuration)

Figure 1:
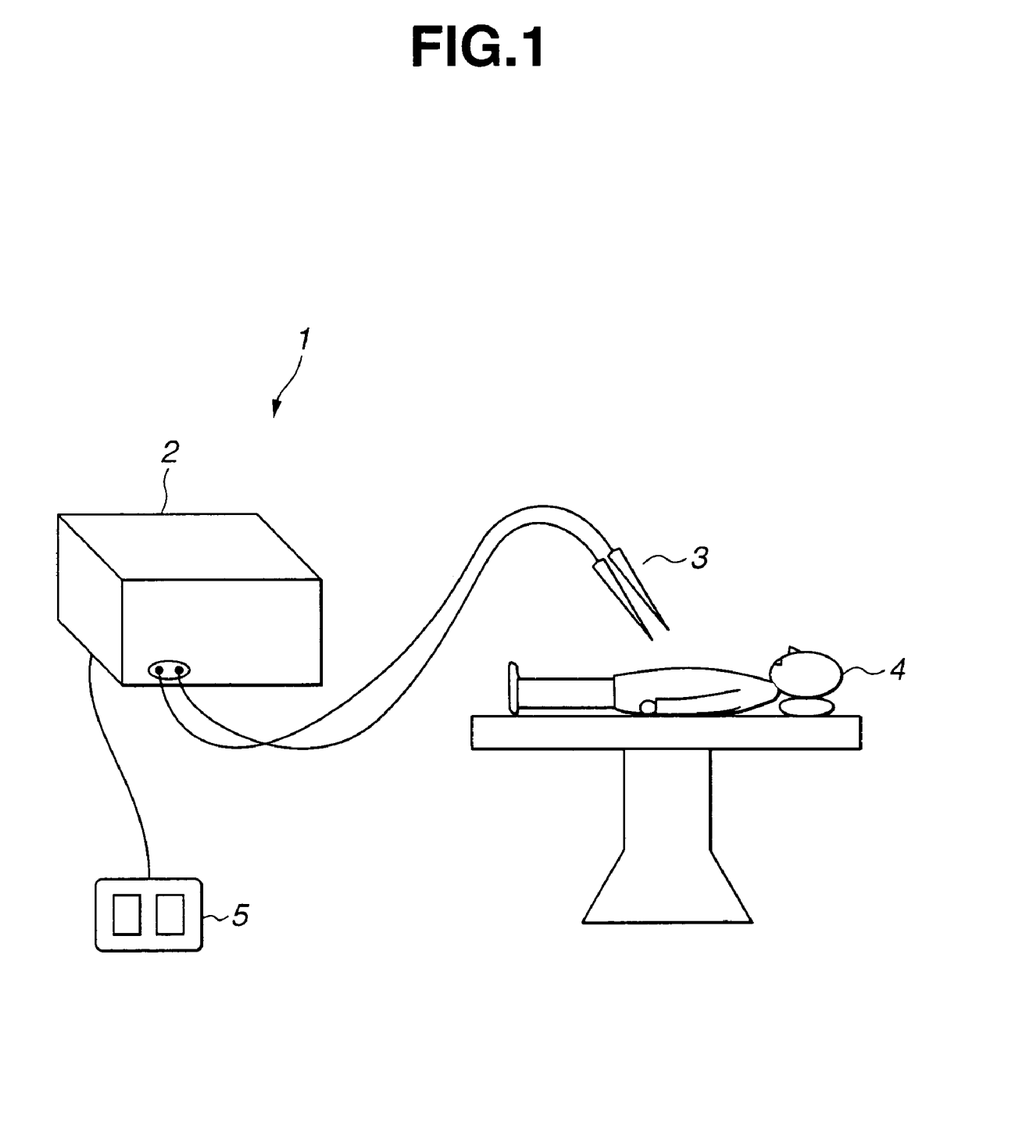
FIG. 1 is a configuration diagram illustrating the configuration of an electric surgery apparatus.

As shown in FIG. 1, an electric surgery apparatus 1 according to the present embodiment has a high frequency cauterizing power supply unit 2 which is connected to a patient 4 via electrodes 3. Furthermore, the high frequency cauterizing power supply unit 2 is connected to a foot switch 5. Note that as for the electrodes 3, either monopolar or multipolar electrodes may be employed.

Figure 2:
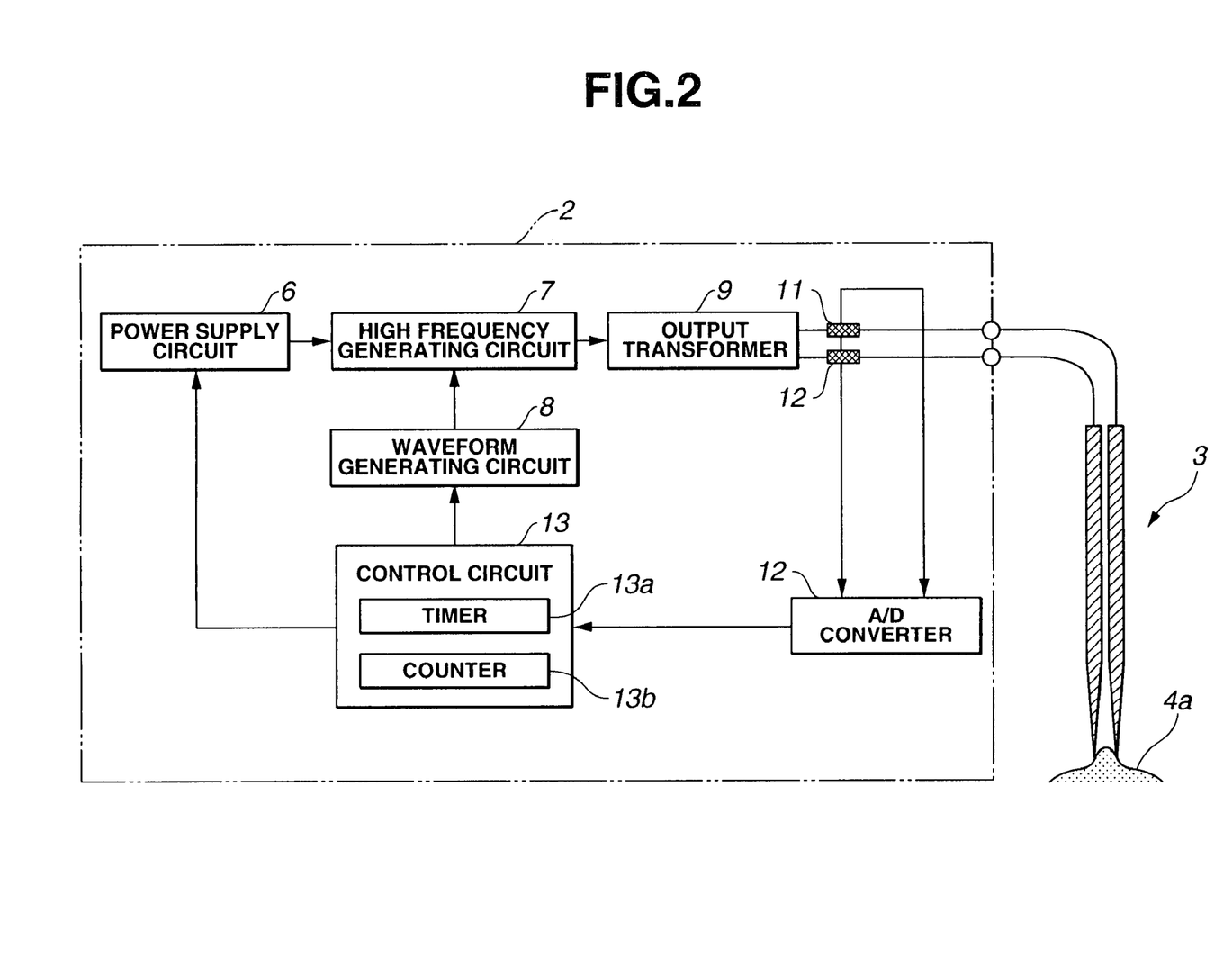
FIG. 2 is a configuration diagram illustrating the configuration of a high frequency cauterizing power supply unit shown in FIG. 1.

As shown in FIG. 2, the high frequency cauterizing power supply unit 2 comprises a power supply circuit 6 for supplying a direct current, a high frequency generating circuit 7 for converting a direct current from the power supply circuit 6 into a high frequency current, a waveform generating circuit 8 for feeding a waveform of a high frequency current to the high frequency generating circuit 7, an output transformer 9 for outputting a high frequency current from the high frequency generating circuit 7 to the electrodes 3, a current sensor 10 for detecting an output current output from the output transformer 9, a voltage sensor 11 for detecting output voltage output from the output transformer 9, an A/D converter 12 for converting analog output signals from the current sensor 10 and the voltage sensor 11 into digital data, and a control circuit 13 for controlling the power supply circuit 6 and the waveform generating circuit 8 based on the digital data from the A/D converter 12.

The control circuit 13 includes a timer 13a for measuring an output period and pause period, and a counter 13b for measuring the number of times of output.

(Operation)

Upon a high frequency power being administered into living-body tissue, the tissue exhibits albuminoid degeneration due to heat, following which moisture within the tissue evaporates and the tissue becomes dry. In this process, the tissue coagulates.

However, in the event that a high frequency power is continuously administered into the dry tissue, the tissue is carbonized and adheres to electrodes of an electric surgery apparatus. In order to prevent the tissue from adhering to the electrodes, administration of a high frequency power into the tissue should be stopped at the time of detecting the drying of tissue.

Figure 3:
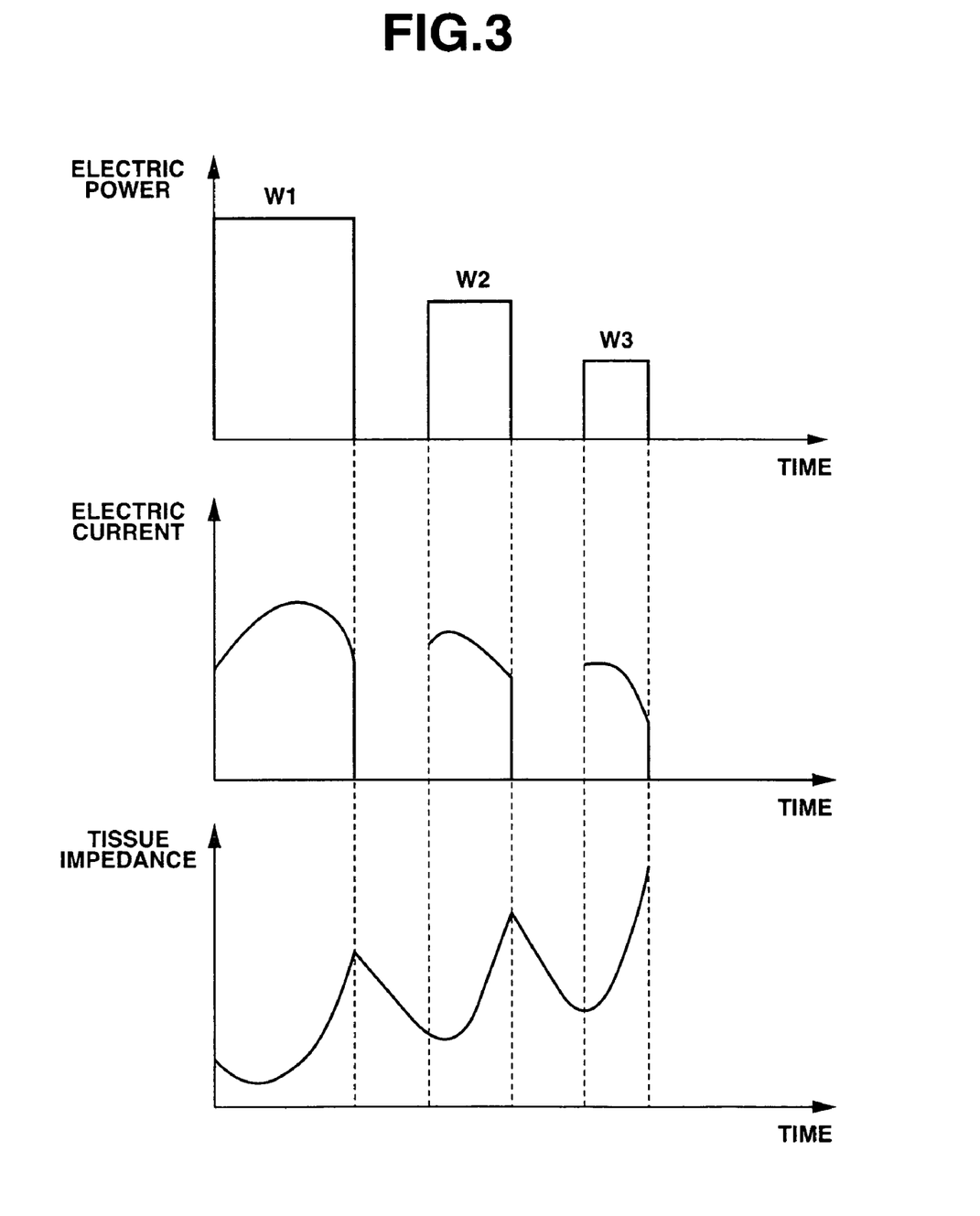
FIG. 3 is an explanatory diagram describing operations at the time of coagulating subject tissue with the electric surgery apparatus shown in FIG. 1.

As shown in FIG. 3, tissue impedance marks a sharp rise when the tissue dries following a temporary drop upon a high frequency power being administered into living-body tissue, and accordingly, the value of a high frequency current exhibits a curve opposite to that of the tissue impedance.

Conventionally, at the time of finding the tissue dry by observing values of tissue impedance and a high frequency current, output of a high frequency power is paused, and at the time of finding that the temperature of the tissue has dropped, the output of the high frequency power is resumed. However, with such a conventional control method, the number of times of output increases in cases of the tissue being small-diameter blood vessels, and the output period becomes prolonged in cases of the tissue being a large-diameter blood vessel due to low power settings, which is time consuming for drying the tissue.

With the present embodiment, the output period is controlled and shortened by detecting in a short time with a simple method the set electric power and number of times of output according to the diameter of a blood vessel.

Figure 4:
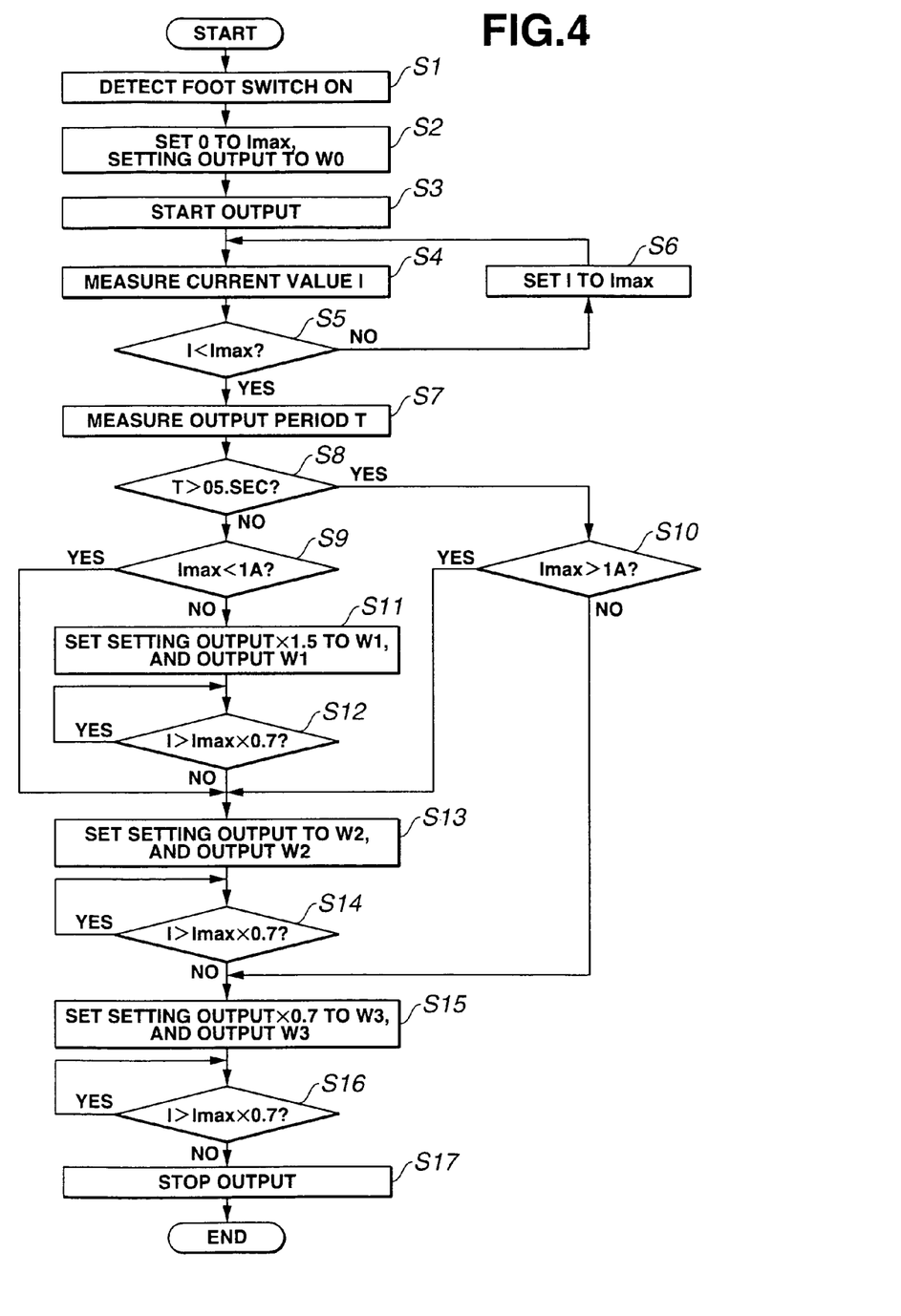
FIG. 4 is a flowchart illustrating the flow for control of the electric surgery apparatus shown in FIG. 1.

Upon the foot switch 5 being stepped on, the control circuit 13 starts control following the flowchart shown in FIG. 4. That is to say, upon detecting in Step S1 that the foot switch 5 is being stepped on, in Step S2, the control circuit 13 sets the maximal high frequency current value Imax to 0 A, the predetermined setting power to a first power W0, and in Step S3, starts output of a high frequency power according to the first power W0.

In Step S4, the control circuit 13 measures signals (current value) received from the current sensor 10 and the voltage sensor 11 via the A/D converter 12, and then stores the measured high frequency current value as I. In Step S5, the control circuit 13 compares the measured high frequency current I with the maximal high frequency current value Imax. In the event that the measured high frequency current I is greater than Imax, the control circuit 13 replaces Imax with I in Step S6, and then returns to Step S4 in order to measure the current again.

Note that the maximal high frequency current value Imax is replaced with the measured current value I in Step S6, however, in the event that output continues, Imax exceeds I, thereby determining Imax.

Next, in Step S7, the control circuit 13 measures time T required for Imax to exceed I with a timer 13a thereof, and then in Step S8, in the event of the measured time T being shorter than 0.5 sec, the flow proceeds to Step S9. In Step S9, in the event that Imax exceeds 1 A, the flow proceeds to Step S11 for treating a large-diameter blood vessel, otherwise, proceeds to Step S13 for treating a middle-diameter blood vessel.

On the other hand, in Step S8, in the event that the measured time T is longer than 0.5 sec, the control circuit 13 proceeds to Step S10, and in Step S10, in the event that Imax exceeds 1 A, the flow proceeds to Step S13 for treating a middle-diameter blood vessel, and otherwise proceeds to Step S15 for treating a small-diameter blood vessel.

In the event that a large-diameter blood vessel is detected in Step S9, in Step S11 the control circuit 13 outputs a second power W1 (=1.5×W0) which is the set output electric power multiplied by 1.5 for example. Next, in Step S12, in the event that I exceeds Imax multiplied by 0.7, i.e., I>Imax×0.7, the flow continues this output while this relation is satisfied, and otherwise proceeds to Step S13, and outputs third power W2 (=W0).

In the event that a middle-diameter blood vessel is detected in Step S9 or Step S10, in Step S13 the control circuit 13 sets the predetermined power value to a third power W2, and outputs this third power W2. Next, in Step S14, the same determination is performed as in Step S12, and in the event that the relation I>Imax×0.7 is not satisfied, in Step S15 the control circuit 13 sets the output power to a fourth power W3, and outputs this fourth power W3 (=0.7×W0).

If a small-diameter blood vessel is detected in Step S10, in Step S15 the control circuit 13 sets the output power to the fourth power W3, and outputs this fourth power w3.

A counter 13b included in the control circuit 13 counts the number of times of output based on the diameter size of the blood vessel. Following Step S15, in Step S16 the same comparison control as Step S12 is performed, and if the relation cannot be satisfied, in other words, if output of W3 finishes, in Step S17, the control circuit 13 stops output of the fourth power W3.

An operator may set the above-described values related to controlling, such as set or compared values. While the above-described control is performed based on a current value, it is needless to mention that the same advantage can be obtained even if tissue impedance, voltages, or the like, are employed instead of a current value.

Figure 5:
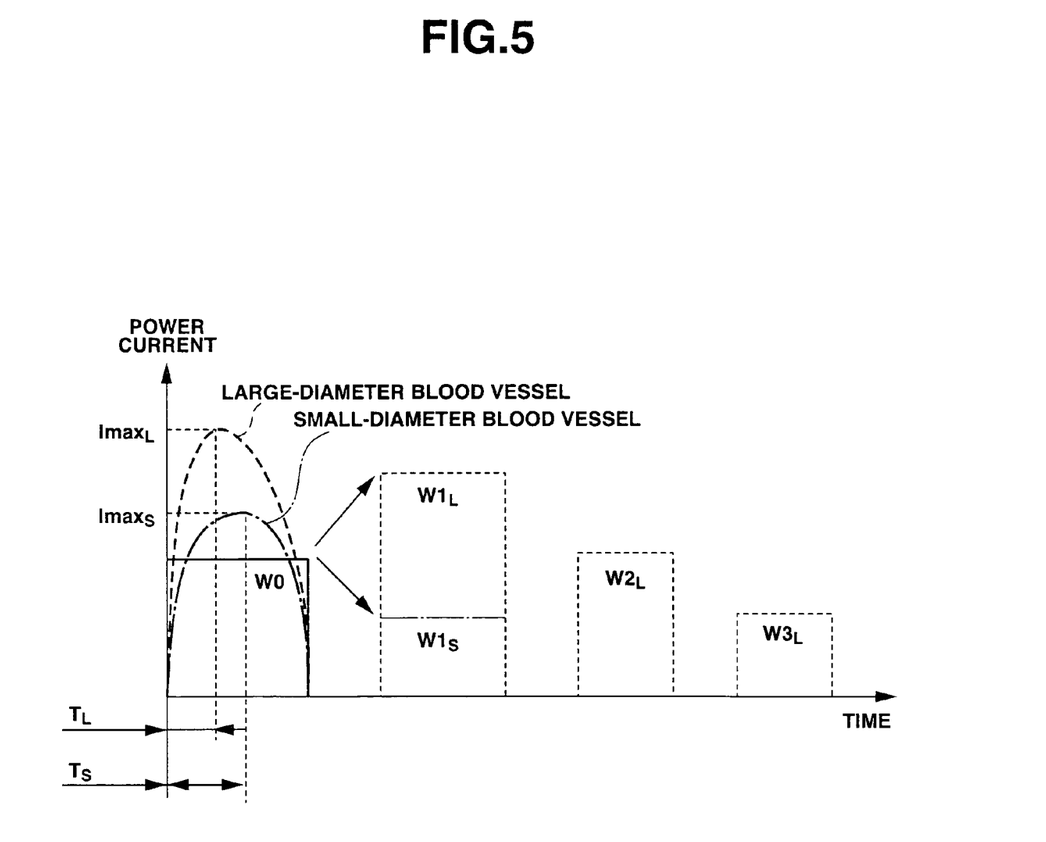
FIG. 5 is an explanatory diagram describing the operations of the electric surgery apparatus shown in FIG. 1.

FIG. 5 illustrates a chart for explaining the operation of the above-described control. The first electric power value W0 is a detecting output value. Following output of an electric power corresponding to W0, the time to reach Imax and the value of Imax determine whether the subject tissue belongs to a large-diameter blood vessel or a small-diameter blood vessel. Thus, as for large-diameter blood vessels, increasing the predetermined output setting power and the number of times of output can yield sufficient force for sealing large-diameter blood vessels. On the other hand, as for small-diameter blood vessels, decreasing the output set electric power and the number of times of output can reduce the output period, thereby preventing wasteful application of energy.

(Effectiveness)

According to the first embodiment of the present invention, the predetermined output setting power and number of times of output are determined depending on the size of the diameter of the blood vessel. Thus, the most appropriate coagulation output to prevent the blood vessel from hemorrhaging can be obtained so as to achieve a minimal output period. In addition, invasion to surrounding tissue other than the position for sealing the blood vessel can be reduced as well as preventing the subject tissue from adhering to electrodes and from carbonizing in order to reduce output period and prevent wasteful energy application.

Moreover, automatic detecting control is performed during the output period, so an operator can simply use this system without troublesome operations. Furthermore, an existing current sensor is employed, thereby enabling a low-cost system to be realized without requiring any new sensors.

Second Embodiment

The second embodiment is almost the same as the first embodiment, so the same reference numerals are applied to the same components, and explanation thereof will be omitted, and only different points will be explained below.

(Configuration)

Figure 6:
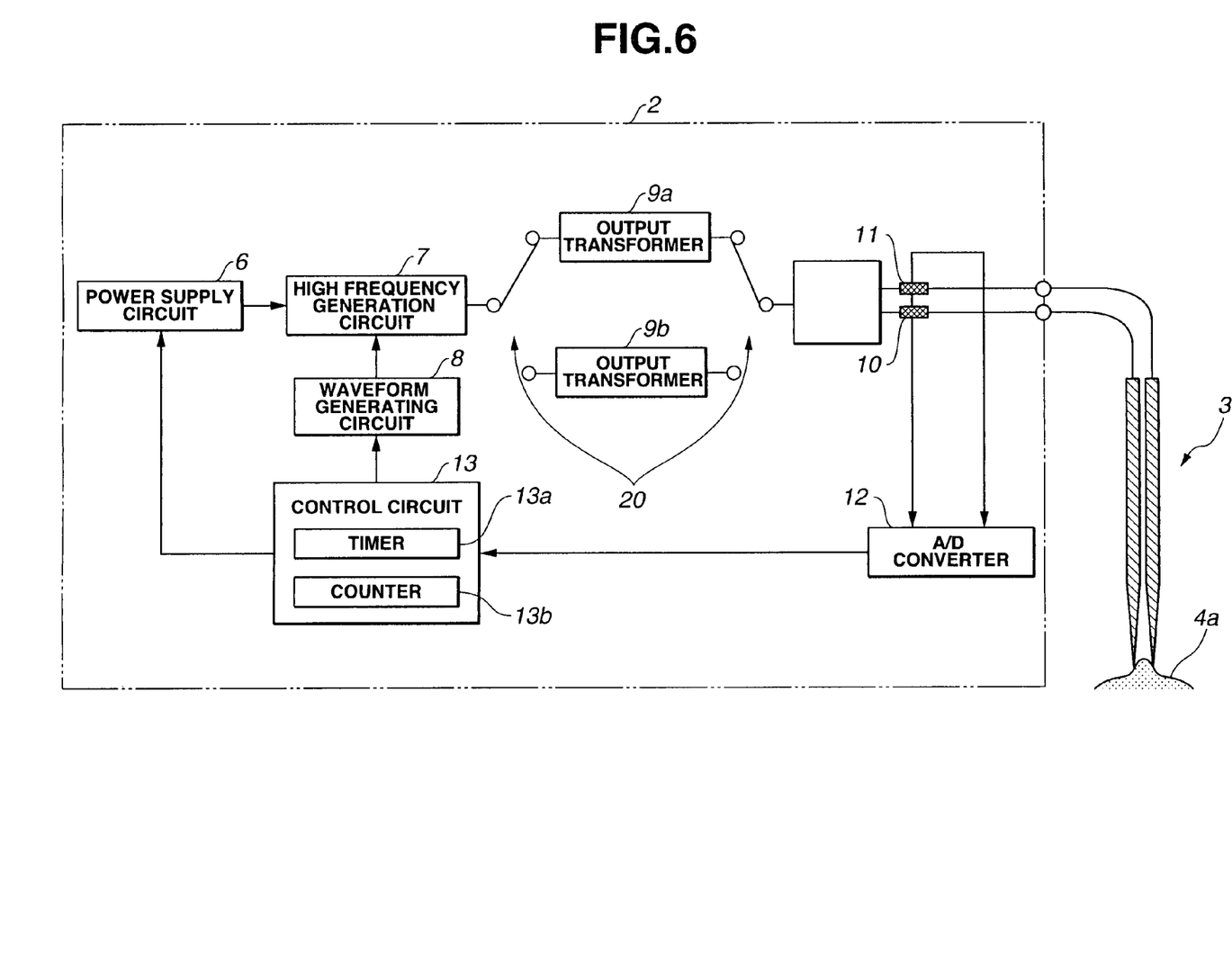
FIG. 6 is a configuration diagram illustrating the configuration of the high frequency cauterizing power supply unit.

As shown in FIG. 6, the high frequency cauterizing power supply unit 2 according to the present embodiment is almost the same as that of the first embodiment, and the difference is that the output transformer 9 is replaced with two output transformers 9a and 9b, and a selector switch 20 for switching these transformers is provided.

(Operations)

Operations up to output processing are the same as those in the first embodiment. However, with the present embodiment, as shown in FIG. 6, the two output transformers 9a and 9b are employed while only one transformer is employed in the first embodiment. The output transformer 9a is for normal use with 100Ω to 2 kΩ, and the output transformer 9b is for handling a low-resistance state with 20Ω to 100 Ω.

The reason to employ the transformer 9b is that there is the need to switch to a low-resistance handling transformer when a resistance value drops, since the output of a transformer generally drops at high and low sides of resistance. In particular, in a case of large-diameter blood vessels, low impedance and a high frequency current is required. However, one transformer alone cannot cover this requirement, so an extra transformer is employed.

Figure 7:
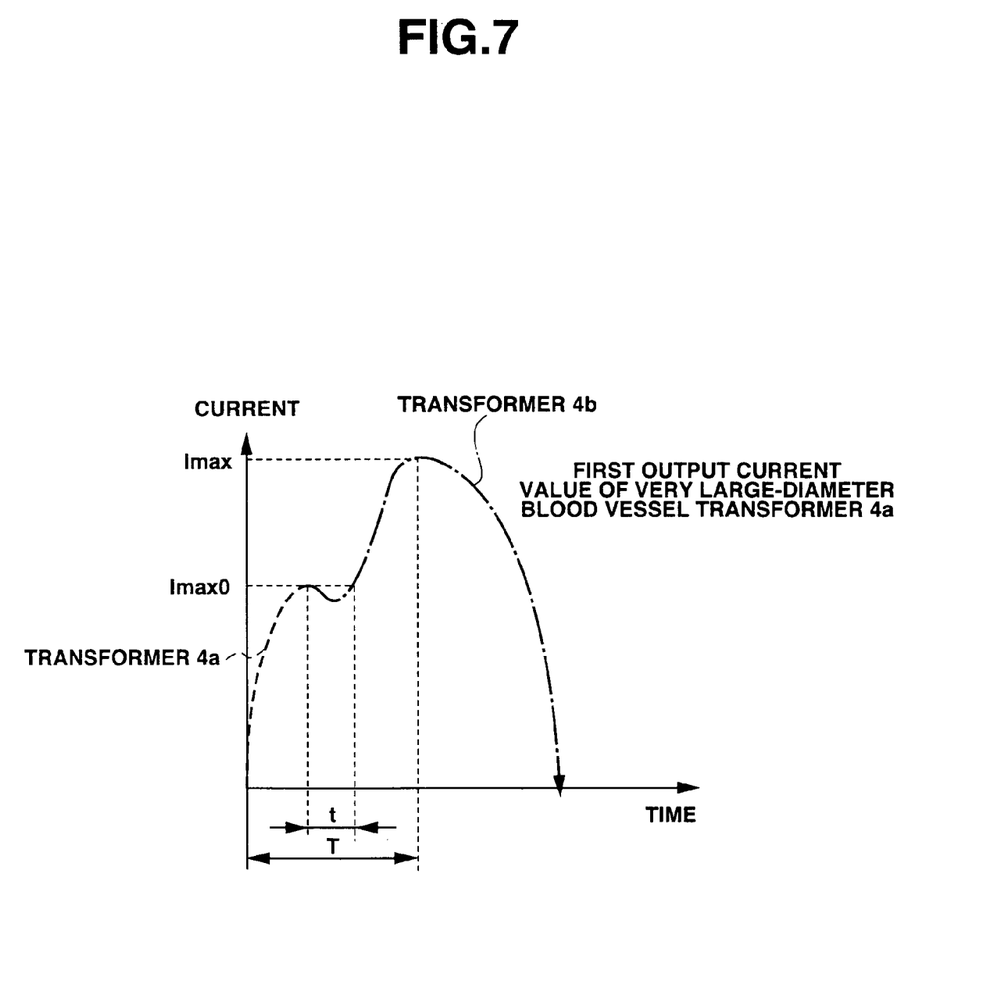
FIG. 7 is an explanatory diagram describing operations of the high frequency cauterizing power supply unit shown in FIG. 6.

Specifically, as shown in FIG. 7, upon output being applied to a very large diameter blood vessel, the transformer 9a for normal use is used at the first output stage. However, upon detecting the resistance dropping to 100Ω or less, the control circuit 13 switches to the transformer 9b for handling low-resistance, using the selector switch 20.

Note that, as shown in the chart in FIG. 5, upon a high frequency current temporally dropping, a "spurious maximal value of high frequency current Imax0" emerges, and also there is the need to consider the transformer switching period t. Accordingly, at the time of switching the transformer, there is the need to ignore the "spurious maximal value of high frequency current Imax0", and also to detect the diameter of the blood vessel based on the obtained value by subtracting the transformer switching period t from the period T up to Imax.

(Effectiveness)

According to the second embodiment of the present invention, eliminating the margin of error generated due to a structural problem of high frequency cauterizing power supply units enables more accurate detection of the diameter of a blood vessel. Output control can be performed for each blood vessel, owing to the improvement of detection accuracy, thereby enabling blood vessels to be sealed in more sure manner.

With the present invention, it is apparent that one skilled in the art can configure various embodiments in a wide range based upon the present invention without departing the spirit and scope of the present invention. This invention is not restricted by any specific embodiment except as limited by the appended claims.

What is claimed is:

1. An electric surgery method comprising:
   generating a high frequency power to treat living-body tissue including blood vessels;
   treating the living-body tissue based on the generated high frequency power;
   converting the high frequency power into intermittent output;
   subcategorizing diameters of blood vessels included in subject tissue by:
      categorizing the blood vessels according to the diameters thereof by detecting the maximal current value flowing to the subject tissue and comparing the time up to the maximal current value with a first threshold value, and
      comparing the maximum current value regarding the categorized blood vessels with a second threshold value; and
   setting output values and the number of times of the intermittent output based on the results of the subcategorizing.

2. An electric surgery method comprising:
   generating a high frequency power;
   treating living-body tissue including blood vessels based on the generated high frequency power;
   subcategorizing diameters of blood vessels included in subject tissue by:
      categorizing the blood vessels according to diameters thereof by detecting the maximal current value flowing to the subject tissue and comparing the time up to the maximal current value with a first threshold value, and
      comparing the maximum current value regarding the categorized blood vessels with a second threshold value;
   setting output values and the number of times of intermittent output based on the results of the subcategorizing; and
   controlling the generated high frequency power based on the settings.

* * * * *